(12) United States Patent
Bodenmiller et al.

(10) Patent No.: US 6,646,749 B2
(45) Date of Patent: Nov. 11, 2003

(54) DEVICE FOR THE MEASUREMENT OF DENTAL OBJECTS

(75) Inventors: Anton Bodenmiller, Leutkirch (DE);
Bernd Breuckmann, Meersburg (DE);
Michael Stocker, Meersburg (DE);
Peter Munstermann, Constance (DE);
Michael Runge, Frickingen (DE)

(73) Assignee: Kaltenbach & Voigt GmbH & Co., Biberach/Riss (DE)

( * ) Notice: Subject to any disclaimer, the term of this patent is extended or adjusted under 35 U.S.C. 154(b) by 0 days.

(21) Appl. No.: 10/107,647

(22) Filed: Mar. 27, 2002

(65) Prior Publication Data

US 2003/0058456 A1 Mar. 27, 2003

(30) Foreign Application Priority Data

Sep. 27, 2001 (DE) ...................................... 201 15 933 U (51) Int. Cl.[7] .............................................. G01B 11/14
(52) U.S. Cl. .................... 356/603; 250/341.6; 433/223; 433/54
(58) Field of Search ................................. 356/603, 622, 356/623, 604, 244, 246; 250/560, 561, 599.22, 334, 341.6; 433/29, 72, 215, 223

(56) References Cited

U.S. PATENT DOCUMENTS 4,641,972 A 2/1987 Halioua et al.
5,386,292 A * 1/1995 Massen et al. ............... 356/376
5,545,039 A * 8/1996 Mushabac .................... 433/215
5,685,084 A * 11/1997 Demers ........................ 433/72
6,264,470 B1 * 7/2001 Jung et al. ..................... 433/29
6,431,871 B1 * 8/2002 Luthardt ....................... 433/223

FOREIGN PATENT DOCUMENTS

| DE | 38 31 217 | * | 3/1990 |
| DE | 195 43 347 A1 | | 5/1997 |
| DE | 298 12 907 U1 | | 9/1999 |
| DE | 198 27 788 | * | 12/1999 |
| DE | 198 38 238 A1 | | 3/2000 |

\* cited by examiner

Primary Examiner—Frank G. Font
Assistant Examiner—Sang H. Nguyen
(74) Attorney, Agent, or Firm—Marshall, Gerstein & Borun LLP (57) ABSTRACT

The invention relates to a device for the optical measurement of dental objects (30) with the use of topometric measurement procedures, having a rotatably mounted object receptacle (18) for holding the object (30) to be measured, a projector (11) for the projection of structured lighting patterns onto the object (30), a detection unit (12) for the detection of lighting structures projected onto the object (30), and an evaluation unit (20) for the calculation of the spatial structure of the object (30) to be measured. In order to improve operability, with the possibility of measuring individual parts of any geometry, the object receptacle (18) is mounted so as to be additionally pivotable around a pivot axis (B) arranged perpendicularly to the axis of rotation (A).

9 Claims, 6 Drawing Sheets

Fig. 7

DEVICE FOR THE MEASUREMENT OF DENTAL OBJECTS

TECHNICAL FIELD

The present invention relates to a device for the optical measurement of dental objects with the use of topometric measurement procedures.

BACKGROUND

In medical technology, dental medicine or dental technology prosthetic parts such as e.g. tooth crowns are being produced to an increasing degree with the aid of computer-supported systems. For this purpose it is initially necessary to produce, as basis for fabrication, a three-dimensional data set of the patient's condition and of the planned prosthetic work in a binary format, which is effected in that the modelled condition—that is for example a plaster stump, model segments, or even a complete model, and the prosthetic work modelled in wax by the dental technician, are measured.

In the meantime, in the manufacture of so-called frameworks, in some cases modelling in wax no longer takes place, but instead the workpiece is constructed by a specially trained dental technician with a 3D CAD system. Here also it is necessary to generate from the initial condition binary data which can then be applied in the computer-supported processing.

For the three-dimensional measurement of objects both mechanical scanning and optical measuring processes and apparatus are employed. In the case of optical measurement systems a distinction is in turn made between scanning processes, which measure the object to be measured point for point, and projection systems, which on the basis of a plurality of overall images of the object determine its three-dimensional structure. In the projection processes, the object to be measured is illuminated with structured light patterns and the projected pattern imaged by an observation system arranged at an angle to the direction of illumination. In accordance with the laws of triangulation, the imaged light structures are then evaluated and processed. Thereby, the object can be illuminated or observed from various directions, whereby from the totality of the images the three-dimensional structure is then calculated. Further, the object to be measured is illuminated with a plurality of lighting patterns, with a certain arrangement, which are for example displaced in phase or have different structures, whereby the accuracy of the optical measurement is significantly increased.

A process of this kind is known from the literature as a so-called phase shift process and is described in detail in U.S. Pat. No. 4,641,972. A further development of this process is disclosed in DE 195 43 347 A1. Thereby, the projection grids employed for the generation of the different lighting structures are arranged on a common carriers with a pre-defined phase relationship, the carrier being pushed into the projection beam in the correct phase. Due to this special arrangement of the projection grids, the structure of the object to be measured can be determined with a very high accuracy.

Further there is known from DE 198 38 238 A1 a device for the computer controlled manufacture of dentures, in which the model of an upper or lower jaw to be measured is mounted on a wedge-shaped object receptacle and is rotated during the measurement.

All previously known optical measurement systems are of relatively complex structure, are mechanically sensitive and for a dental technician can be operated only with difficulty. Thus, there is a need for an optical 3D measurement system which can be readily operated by persons involved in dental medicine and which can measure individual dental parts of any geometry.

BRIEF DESCRIPTION OF THE DRAWINGS

Below, the invention will be described in more detail with the reference to the accompanying drawings, which show.

DETAILED DESCRIPTION

A device for the optical measurement of dental objects has a rotatably mounted object receptacle for holding the object to be measured, a projector for the projection of structured lighting patterns onto the object, a detection unit for the detection of the lighting structures protected onto the object, and an evaluation unit for calculation of the spatial structure of the object to be measured. In accordance with the invention, the object receptacle is additionally mounted to be pivotable about a pivot axis arranged perpendicularly to the axis of rotation. By means of the rotation/pivoting arrangement thereby realised, it is ensured that also undercuts on the object to be measured, such as appear for example if a crown is to produced below the equator, or if a crown rim or an inlay is to be produced in a case preparation (i.e. with opposing or parallel walls which provide a good friction engagement and therefore a good anchor), can be reliably measured. Furthermore, the possibility is available to freely program the movements of the object receptacle, and thus of the object to be measured, during the measurement procedure, or to employ pre-programmed movement sequences corresponding to the structure of the object, which sequences can be called up by the user in a simple manner.

The useability of the system can be improved if the object receptacle is removable from the rotation/pivoting unit so that the object to be measured can be mounted thereon outside of the measurement chamber at any desired work station. The preferably plate-like object receptacle may then have a pattern of bores for the attachment of retaining means for the secure holding of the object to be measured. Preferably this pattern of bores is honeycomb-like.

The procedures to be carried out by the operating person can be further simplified in that the projector for the generation of the projection pattern and the detection unit, which may be for example a CCD camera, are arranged on a common stand and fixably directed relative to one another. The arrangement of the projector in the detection unit is thus determined in advance and need not be newly set in each case by the operating person.

Figure 1:
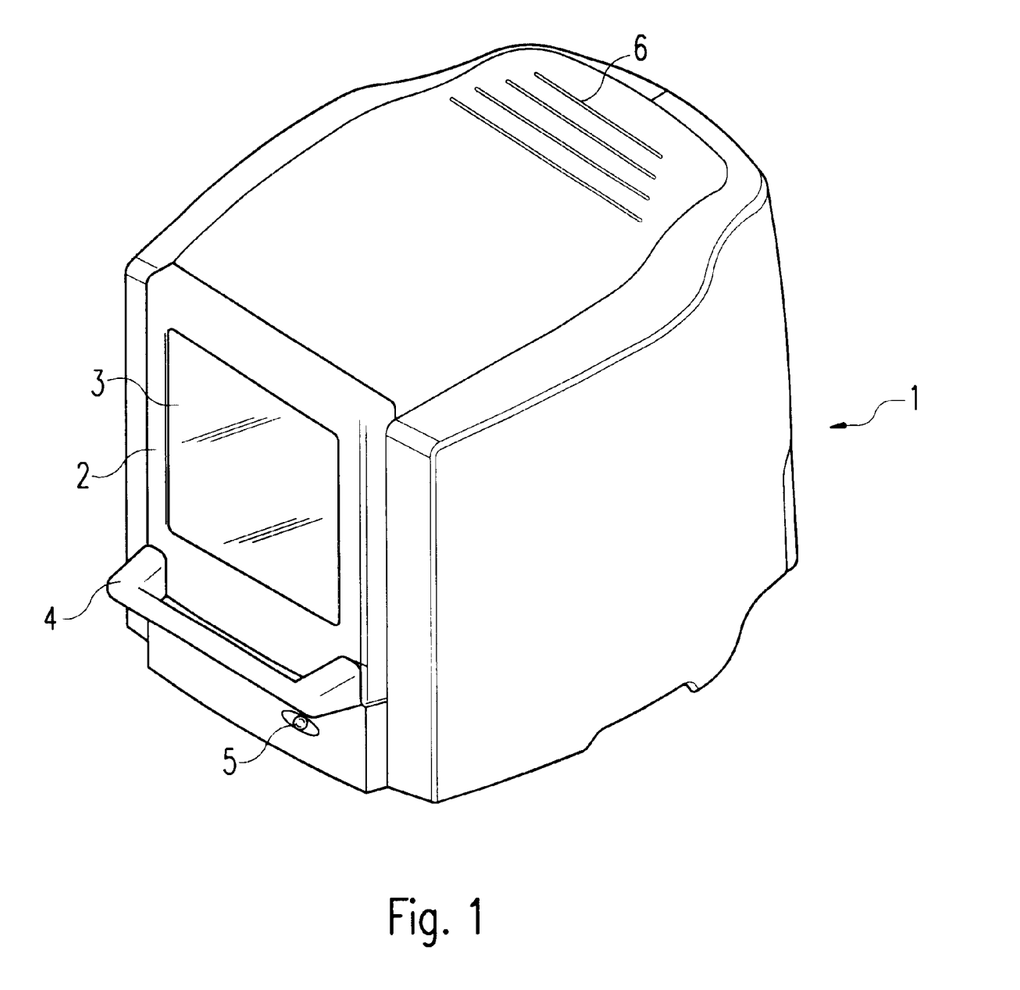
FIG. 1 an external view of the device in accordance with the invention, with closed front door.

The optical measurement device in accordance with the invention is arranged within a box-like housing 1 illustrated in FIG. 1, which housing is closed at its forward side with a door which can be swung away upwardly.

The door, which can be operated with a grip 4, has a viewing window 3, having a grey matted plexiglass pane, by way of which the measurement procedure can be observed. Below the door 2 there is arranged on the front side of the housing 1 an LED 5 which indicates the current operational condition of the measurement device. A permanently illuminated LED signals for example operational readiness, whereas in contrast a blinking indicates that a measurement procedure is now running. A flashing of the LED, in contrast, signals the occurrence of a fault.

On the upper side of the housing 1 there are arranged in the rear region a plurality of ventilation slots 6 through which air heated by electronic apparatuses arranged within the housing 1 can be taken away to the exterior.

Figure 2:
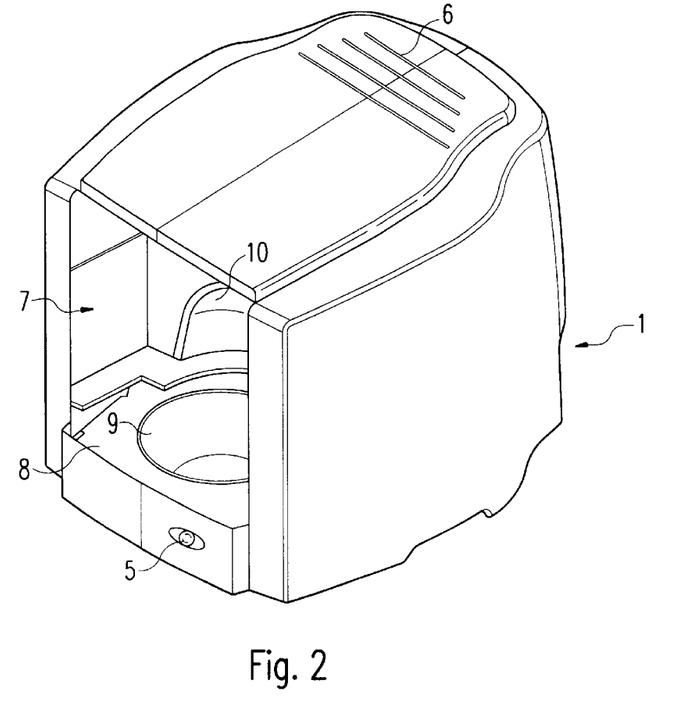
FIG. 2 the external view of the measurement device with removed front door.
Figure 3:
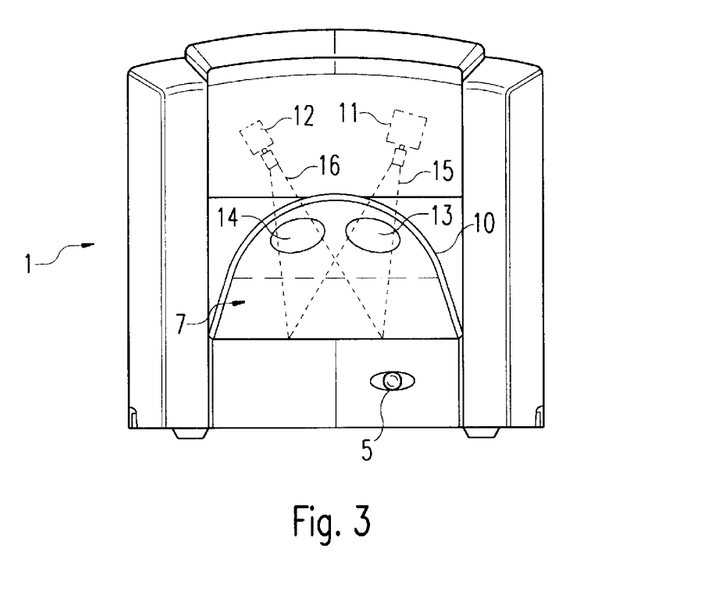
FIG. 3 the interior view of the measurement chamber.

As can be understood from the illustrations in FIGS. 2 and 3, access is obtained to the measurement chamber 7 within the housing 1 through the (now non-illustrated) door, in which measurement chamber the object to be measured is to be arranged. The retaining of the object receptacle, explained in more detail below, is effected in a base part 8 which has in a forward region a recess 9 in the shape of a hemisphere, into which a rotation/pivoting unit holding the object receptacle is placed.

By means of a protective dividing wall 10, which in its rearward region is formed in the shape of a dome, the measurement chamber 7 is separated off from the rearward region of the housing 1 in which inter alia a projector 11 and a camera 12 are arranged. An optical contact between these two apparatuses and the object to be measured exists only via two openings 13 and 14 placed in the protective dividing wall 10. By means of the arrangement of the projector 11 and of the camera 12, and of the two openings 13 and 14, an illumination cone 15 and an observation cone 16 are defined, which overlap in the region in which the object to be measured is arranged. By these means there is attained an optimum measurement of the object with at the same time the greatest possible protection from external influences.

Figure 4:
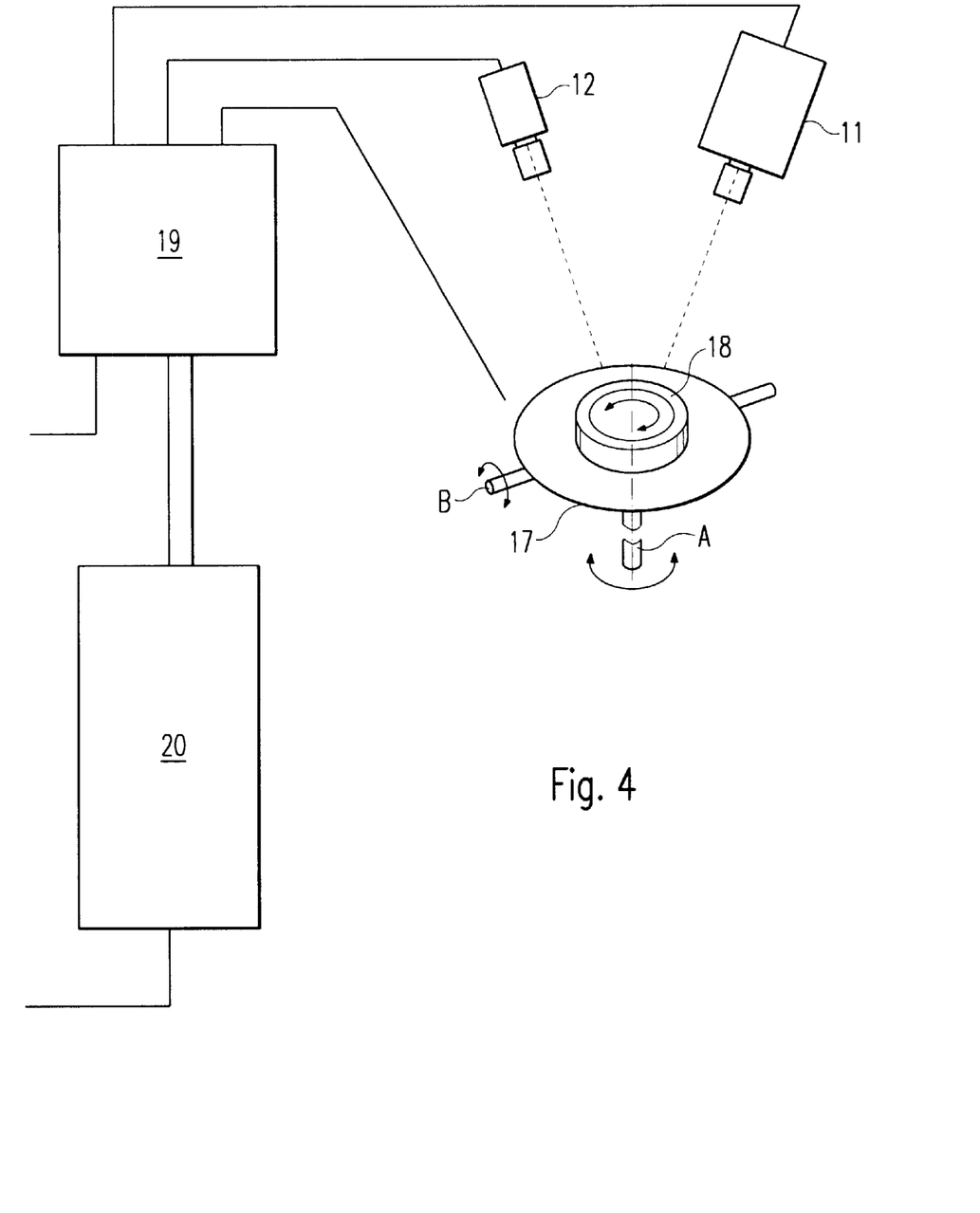
FIG. 4 a schematic illustration of the measurement system.

FIG. 4 shows the schematic construction of the overall measurement device. The main elements of the measurement system are the projection unit 11, the CCD camera 12 and the rotation/pivoting unit 17, on which the object receptacle 18 holding the object to be measured is mounted. The rotation/pivoting unit 17 is formed of two rotary axes A and B coupled with one another, whereby the drive of the two axes A and B upon measurement of the object arranged on the object receptacle 18 is effected by means of stepping motors. This arrangement thus makes possible the simultaneous rotation and tilting of the object receptacle 18, so that also geometries having undercuts can be reliably detected. In order to be able to fully exploit the possibilities for adjustment, the rotation/pivoting unit 17 and the object receptacle 18 are so configured that the middle point of the object to be measured lies approximately at the level of the tilt axis B.

The measurement of the object is effected for example by the process described in U.S. Pat. No. 4,641,972. Thereby, with the aid of the projector 11, a lighting pattern—for example a stripe pattern—is projected. The lighting pattern deformed on the surface of the object is then imaged with the aid of the camera 12 and evaluated, whereby due to the known arrangement of the projector 11 and the camera 12 with respect to the object to be measured, with the aid of calculations which are set out in detail in U.S. Pat. No. 4,641,972, the coordinates of the surface of the object to be measured can be calculated. Such image producing triangulation methods are already sufficiently well known and therefore will not be described here in more detail. By means of a rotation and tilting of the object there are taken in the present case images from different directions, so that the data obtained thereby can in the end be combined to the three-dimensional overall structure. Analogously to the method described in DE 195 43 347 A1, with an arrangement of the object to be measured which remains unchanged, different lightning patterns with defined phase relationships can be projected one after another onto the object. The control of the projector 11, the camera 12 and the rotation/pivoting unit 17 is effected via a suitable control unit 19, which passes on the images detected by the camera 12 to a computer 20 of an image and data processing system.

A significant feature of the device in accordance with the invention is that the projector 11 and the camera 12 are arranged on a common stand and so aligned with respect to one another that their optical axes intersect in the middle point of the object receptacle 18. This fixedly predetermined arrangement of the various elements of the measurement system on the one hand facilitates handling and on the other hand guarantees an optimum measurement of the object. The movements carried out by the rotation/pivoting unit 17 during the measurement of the object are freely programmable and can be newly set before each measurement to be carried out. Preferably, particular pre-set movement sequences, depending upon the kind of the object to be measured, are fixed in the form of macros, which can then be called up in a simple manner. This also contributes to the simplification of the handling of the overall system.

Figure 5:
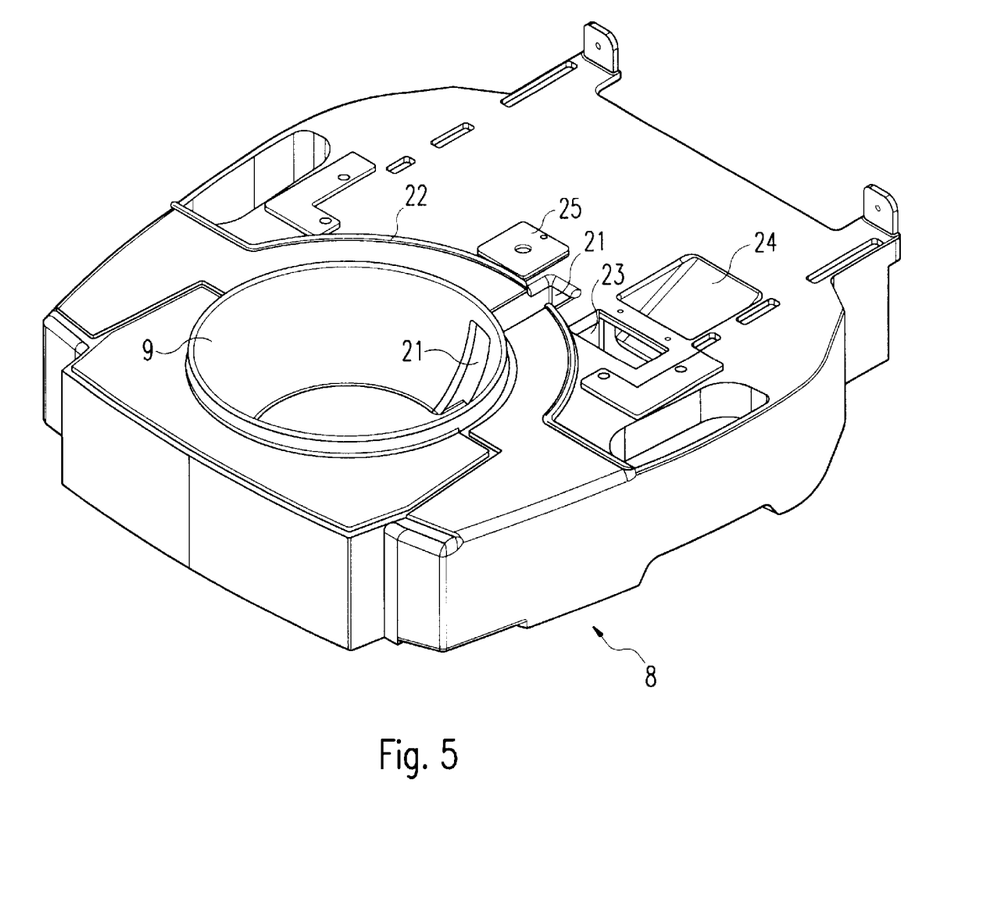
FIG. 5 the base element of the measurement device.

FIG. 5 shows the base part 8, formed of a cast aluminium part, of the measurement device with the hemispherical mounting recess 9 for the rotation/pivoting unit. At the rear side of the base part 8 there are located the (non-illustrated) connections for the current supply and the interface to the computer of the image and data processing system. On the rear side of the mounting recess 9 for the rotation/pivoting unit there is located a cable channel 21 for the control and current lines of the stepping motors of the rotation/pivoting unit. A rib 22 on the upper side of the base part 8 bounds the forward measurement region. From this rib 22 there extends upwardly the protective dividing wall illustrated in FIG. 3 in order to separate the measurement chamber from the electronics zone therebehind.

For cooling the apparatuses arranged in the rearward electronics zone there is employed a non-illustrated electronic fan, which is emplaced in an installation hole 23 of the base part 8. From this installation hole 23 there extends rearwardly a distribution channel 24 through which the cooling air flow generated by the fan is so send out that a part of the cooling air passes over the electronics and thereby above all cools the projector. The remaining quantity of the cooling air flows to the measurement chamber. The heated air is discharged to the exterior through the ventilation slots 6 arranged in the rearward region of the housing 1. An air filter may be arranged before the fan on the suction side, whereby the entry of dust particles into the measurement chamber is prevented.

The stand is mounted on a bearing surface 25 and at the upper end of the stand the light stripe projector 11 and the camera 12 are arranged on an inclined adjustment surface. The camera 12 is connected with the optical evaluation system preferably via a firewire interface which makes possible a high data transfer rate.

Figure 6:
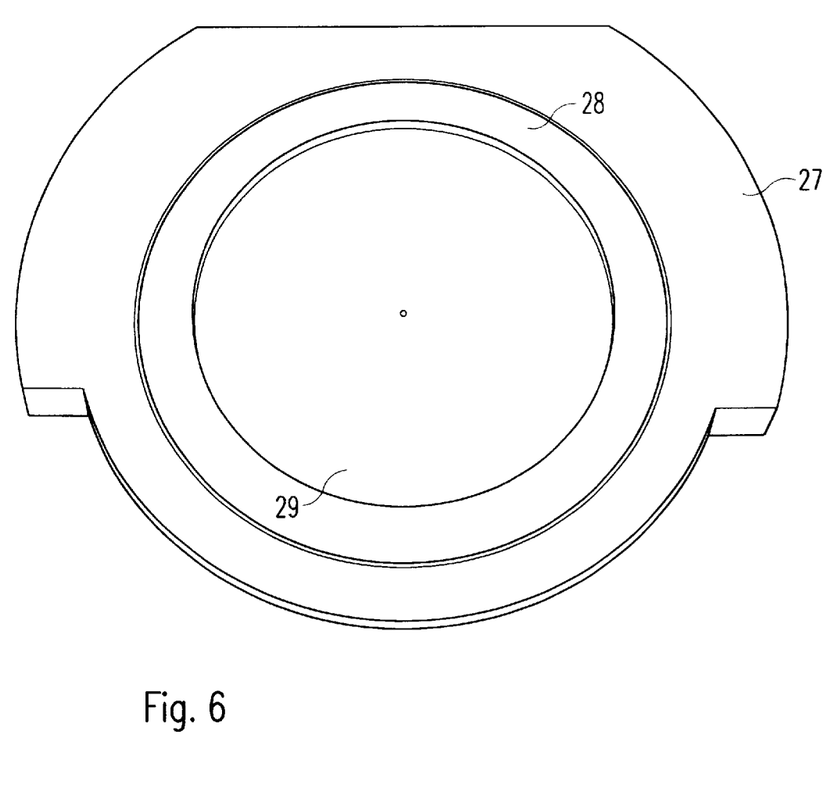
FIG. 6 the object receptacle in a removed condition.

The installation of the rotation/pivoting unit in the base part 8 is effected with the aid of a bearing ring 27 which is illustrated in FIG. 6. On the underside of the bearing ring 27, which is placed on the forward region of the base part 8, there is located the axis arrangement and the stepping motors for control of the movement sequences of the object receptacle. In the middle of the bearing ring 27 there is arranged a measurement plate 28, which is rotated and pivoted in the manner described above via the stepping motors.

The measurement plate 28 has a plate-like recess 29 into which the object receptacle in the form of a measurement insert, can be placed. The object receptacle 18 is provided with a honeycomb-like pattern of bores 31 which allows the insertion of holder pins 32 as desired, and the insertion of a clamping device 33 for retaining the object to be measured. In this manner dental technical models and objects of any form can be reliably fixed. In particular there exists the possibility to effect to the fixing of the object to be measured on the object receptacle 18 outside of the housing 1 at any desired work station or room.

The separation between the measurement plate 28 and the object receptacle 18 further offers the possibility of loading a plurality of object receptacles 18. These may then be placed in the measurement device at a suitable point in time and measured. Further, the pattern of bores 31 allows specific holding devices for the measurement of individual teeth or of models to be screwed in.

Figure 7:
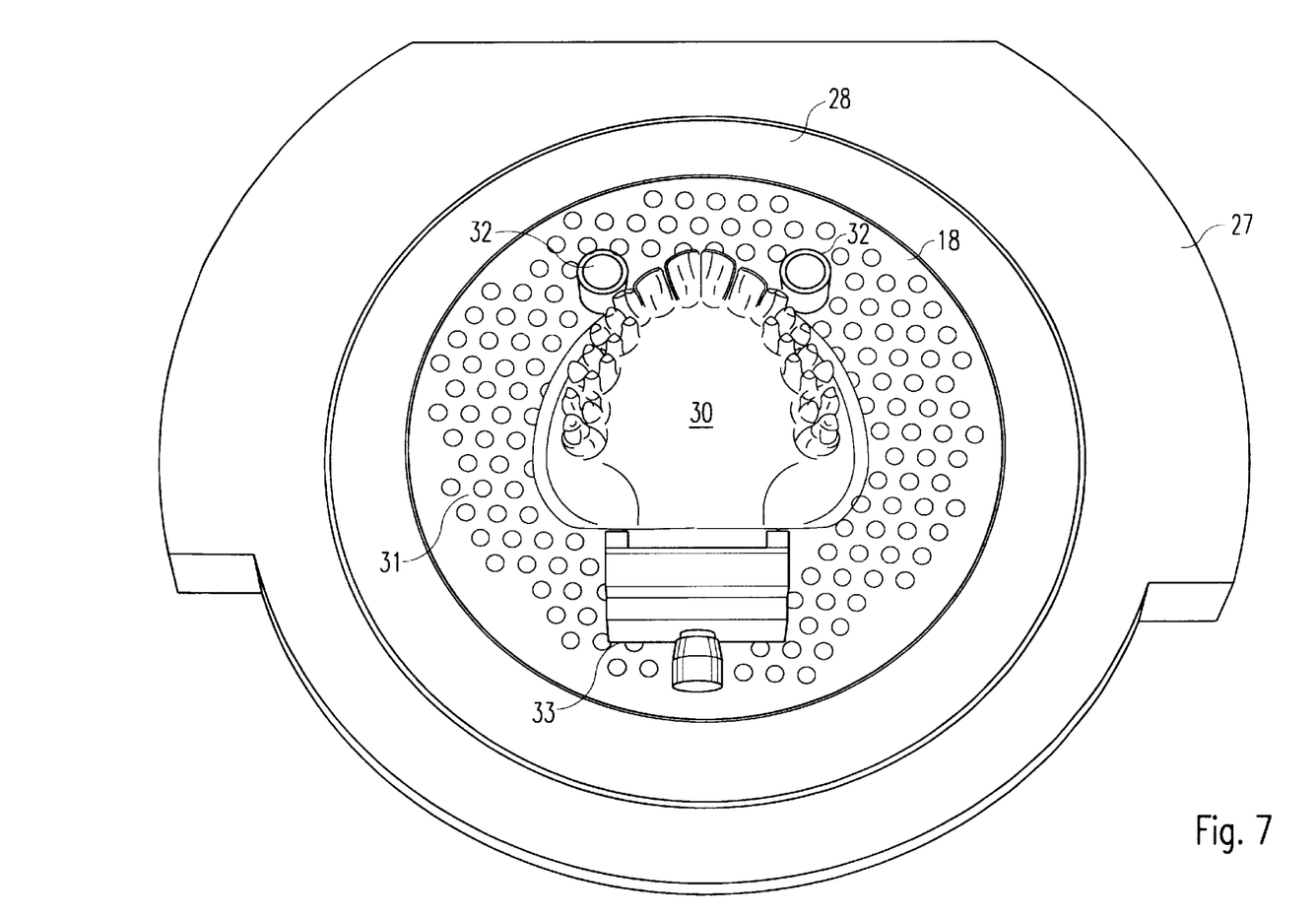
FIG. 7 an equipped object receptacle.

The object receptacle 18, with the object 30 to be measured mounted thereon, is then placed into the measurement plate 28, so that the arrangement illustrated in FIG. 7 is provided. Though the matching size of the recess 29 of the measurement plate 28 there is provided a defined bearing surface for the object receptacle 18 so that operating errors are virtually excluded. As is illustrated in FIG. 7, by means of the free arrangement of the holding means, virtually any measurement object 30 can be fixed and measured. Thereby, the object receptacle 18 is so arranged within the rotation/pivoting unit that the object 30 to be measured is mounted substantially at the level of the pivot axis. By these means, the adjustment possibilities of the rotation/pivoting unit can be fully exploited, so that an optical measurement of the object 30 is made possible.

The measurement device in accordance with the invention is thus simply operable also for persons from other specialist fields—such as for example medical technology, dental medicine or dental technology. Through the possibility of pivoting the object to measured, in addition to rotation thereof, even very complicated structures, can be reliably and accurately measured.

What is claimed is:

1. Device for optically measuring dental objects with topometric measurement procedures, comprising
    an object receptacle for holding an object to be measured, said object receptacle being mounted for rotation about an axis (A),
    a projector for projecting structured lighting patterns onto the object,
    a detection unit for detecting lighting structures projected onto the object, and
    an evaluation unit for calculating spatial structure of the object to be measured;
    wherein the object receptacle is mounted so as to be pivotable around a pivot axis (B) disposed perpendicularly to the axis of rotation (A) and has a pattern of bores for the attachment of means for retaining the object.

2. Device according to claim 1, comprising a rotation/pivoting unit from which the object receptacle is removable.

3. Device according to claim 1, wherein the object receptacle is plate-like.

4. Device according to claim 1, wherein the pattern of bores is honeycomb-like.

5. Device according to claim 1, wherein the object to be measured is mountable substantially at the level of the pivot axis (B).

6. Device according to claim 1, wherein the projector and the detection unit are disposed on a common stand.

7. Device according to claims 6, wherein the projector and the detection unit are aligned with each other.

8. Device according to claim 1, wherein the movement patterns of the object receptacle during the measurement procedure are freely programmable.

9. Device according to claim 1, wherein by means of a control device pre-programmed movement sequences for the object receptacle can be called up during the measurement procedure.

* * * * *

UNITED STATES PATENT AND TRADEMARK OFFICE
CERTIFICATE OF CORRECTION

PATENT NO. : 6,646,749 B2
DATED : November 11, 2003
INVENTOR(S) : Anton Bodenmiller et al.

It is certified that error appears in the above-identified patent and that said Letters Patent is hereby corrected as shown below:

Title page,
Item [75], Inventors, please delete "Constance" and insert -- Konstanz --.
Item [57], ABSTRACT, please delete "The invention relates to a device for the optical measurement of dental objects (30) with the use of topometric measurement procedures, having a rotatably mounted object receptacle (18) for holding the object (30) to be measured, a projector for the projection of structured lighting patterns onto the object (30), a detection unit (12) for the detection of lighting structures projected onto the object (30), and an evaluation unit (20) for the calculation of the spatial structure of the object (30) to be measured. In order to improve operability, with the possibility of measuring individual parts of any geometry, the object receptacle (18) is mounted so as to be additionally pivotable around a pivot axis (B) arranged perpendicularly to the axis of rotation (A)." and insert -- The invention relates to a device for the optical measurement of dental objects with the use of topometric measurement procedures, having a rotatably mounted object receptacle for holding the object to be measured, a projector for the projection of structured lighting patterns onto the object, a detection unit for the detection of lighting structures projected onto the object, and an evaluation unit for the calculation of the spatial structure of the object to be measured. In order to improve operability, with the possibility of measuring individual parts of any geometry, the object receptacle is mounted so as to be additionally pivotable around a pivot axis (B) arranged perpendicularly to the axis of rotation (A). --

Column 6,
Line 34, please delete the phrase "Device according to claims 6," and insert -- Device according to claim 6, --

Signed and Sealed this

Twenty-fifth Day of May, 2004

JON W. DUDAS
*Acting Director of the United States Patent and Trademark Office*